(12) United States Patent
Ouchi

(10) Patent No.: US 6,193,717 B1
(45) Date of Patent: *Feb. 27, 2001

(54) TREATING INSTRUMENT FOR ENDOSCOPE

(75) Inventor: Teruo Ouchi, Saitama (JP)

(73) Assignee: Asahi Kogaku Kogyo Kabushiki Kaisha, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/156,765

(22) Filed: Sep. 18, 1998

(30) Foreign Application Priority Data

Oct. 16, 1997 (JP) .................................................. 9-283212
Oct. 16, 1997 (JP) .................................................. 9-283213

(51) Int. Cl.⁷ .................................................. A61B 18/14
(52) U.S. Cl. .................................. 606/49; 606/46; 606/47; 604/21; 604/114
(58) Field of Search ................. 606/45, 46, 49, 606/41, 47, 48, 50; 607/105, 113; 604/21, 114

(56) References Cited

U.S. PATENT DOCUMENTS

| 4,222,380 | 9/1980 | Terayama . | |
|---|---|---|---|
| 4,311,143 | * 1/1982 | Komiya | 606/47 |
| 4,708,137 | * 11/1987 | Tsukagoshi | 606/46 |
| 4,857,057 | 8/1989 | Sanagi . | |
| 5,403,311 | * 4/1995 | Abele et al. | 606/49 |
| 5,441,499 | * 8/1995 | Fritzsch | 606/45 |
| 5,522,815 | * 6/1996 | Durgin, Jr. et al. | 606/50 |
| 6,048,340 | * 4/2000 | Miyagi | 606/46 |

FOREIGN PATENT DOCUMENTS

| 0704189 | 4/1996 | (EP) . |
|---|---|---|
| 62-213749 | 9/1987 | (JP) . |
| 5-5106 | 1/1993 | (JP) . |
| 5-57021 | 3/1993 | (JP) . |

* cited by examiner

*Primary Examiner*—Lee Cohen
(74) *Attorney, Agent, or Firm*—Greenblum & Bernstein, P.L.C.

(57) ABSTRACT

A flexible sheath is removably inserted into an instrument-inserting channel of an endoscope. A treating member for applying a treatment to mucous membrane in a body cavity is projected from and withdrawn into the distal end of the sheath by an operation conducted at the proximal end of the sheath. An exposed electrode is provided at the distal end surface of the sheath. An electrically conductive member extending through the sheath is electrically connected at a distal end thereof to the electrode and at a proximal end thereof to a high-frequency power supply at the proximal end of the sheath.

4 Claims, 8 Drawing Sheets

TREATING INSTRUMENT FOR ENDOSCOPE

BACKGROUND OF THE INVENTION

The present disclosure relates to subject matter contained in Japanese Patent Application No. 9-283212 (filed on Oct. 16, 1997) and Japanese Patent Application No. 9-283213 (filed on Oct. 16, 1997), which are expressly incorporated herein by reference in their entireties.

1. Field of the Invention

The present invention relates to a treating instrument used through an instrument-inserting channel of an endoscope.

2. Description of the Prior Art

There are various instruments used with endoscopes. Syringes are used, for example, to inject a liquid medicine into the mucous membrane in a body cavity. High-frequency snares are used, for example, to excise polyps from the mucous membrane surface. These instruments are arranged such that a treating member, i.e. a syringe needle or a snare wire, used to apply a treatment to the mucous membrane in the body cavity projects from and withdraws into the distal end of a sheath removably inserted into an instrument-inserting channel of an endoscope.

When such a syringe for an endoscope is used to give an injection into the mucous membrane in a body cavity, there may be bleeding from a hole opening after the needle has been pulled out. In the case of removal of a polyp with a high-frequency snare, there may also be bleeding from the cut end of the mucous membrane surface.

In such a case, if a large amount of blood is lost through the bleeding because the blood vessel as a bleeding source is thick, the bleeding itself is dangerous. Even when the amount of blood lost is not so large, as the time proceeds, the endoscopic observation may become impossible to perform due to the bleeding. In such a case, it is difficult to continue the endoscopic examination.

SUMMARY OF THE INVENTION

An object of the present invention is to provide a treating instrument for an endoscope that is capable of preventing bleeding after an endoscopic treatment.

Other objects and advantages of the present invention will become apparent from the following detailed description of illustrated embodiments of the invention.

According to the present invention, there is provided a treating instrument for an endoscope that includes a flexible sheath removably inserted into an instrument-inserting channel of the endoscope. A flexible fluid transfer tube is axially movably inserted in the sheath. A syringe needle is provided at the distal end of the fluid transfer tube. The needle is made of an electrically conductive material. The needle is projected from and withdrawn into the distal end of the sheath by axially moving the fluid transfer tube from the proximal end thereof. An electrically conductive member extends through the sheath without electrically conducting to the surface of the sheath. The electrically conductive member is electrically connected at a distal end thereof to the needle and connected at a proximal end thereof to a high-frequency power supply at the proximal end of the sheath.

In addition, there is provided a treating instrument for an endoscope that includes a flexible sheath removably inserted into an instrument-inserting channel of the endoscope. The outer surface of the sheath is formed from an electrically insulating tube. The treating instrument further includes a treating member for applying a treatment to mucous membrane in a body cavity. The treating member is projected from and withdrawn into the distal end of the sheath by an operation conducted at the proximal end of the sheath. An exposed electrode is provided at the distal end surface of the sheath. An electrically conductive member extends through the sheath without electrically conducting to the surface of the sheath. The electrically conductive member is electrically connected at a distal end thereof to the electrode and connected at a proximal end thereof to a high-frequency power supply at the proximal end of the sheath.

BRIEF DESCRIPTION OF THE DRAWINGS

The present invention may be more fully understood from the description of preferred embodiments of the invention set forth below, together with the accompanying drawings, in which.

DESCRIPTION OF THE EMBODIMENTS

Embodiments of the present invention will be described below with reference to the accompanying drawings.

Figure 1:
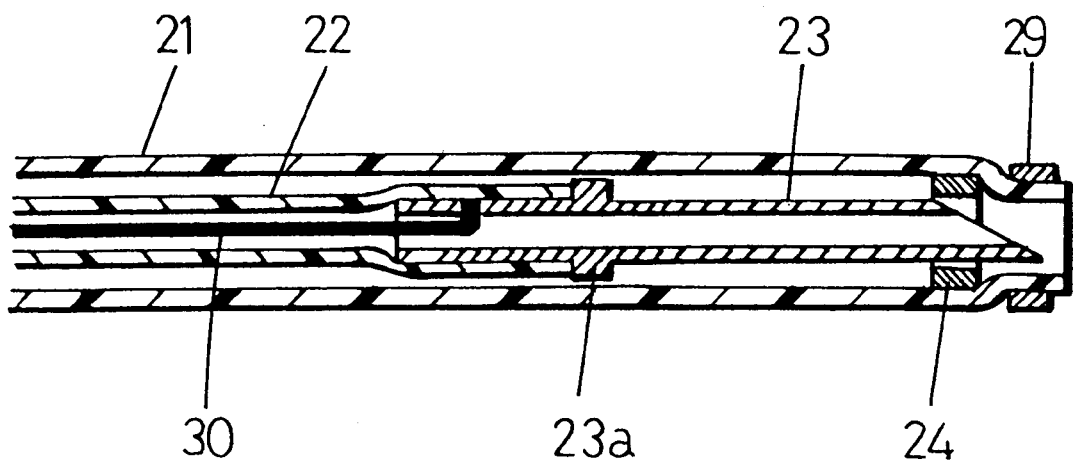
FIG. 1 is a sectional side view of a distal end portion of a syringe for an endoscope according to a first embodiment of the present invention, showing a state where a needle is withdrawn into the distal end of a sheath.
Figure 2:
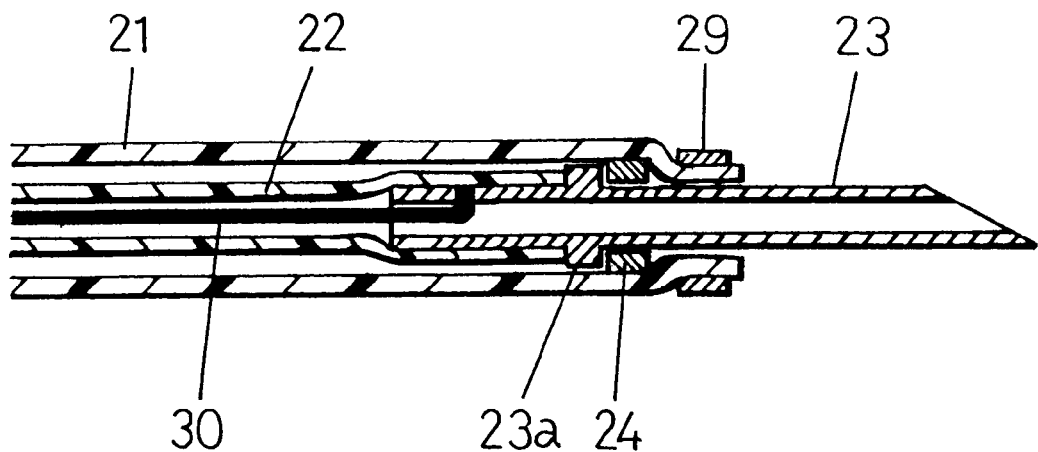
FIG. 2 is a sectional side view of the distal end portion of the syringe according to the first embodiment of the present invention, showing a state where the needle projects from the distal end of the sheath.

FIGS. 1 and 2 show a distal end portion of a syringe for an endoscope. FIG. 1 shows the syringe in a state where a needle 23 is withdrawn into a sheath 21. FIG. 2 shows the syringe in a state where the needle 23 projects from the distal end of the sheath 21.

The sheath 21 is removably inserted into an instrument-inserting channel of an endoscope (not shown). The sheath 21 is formed from an electrically insulating flexible tube, for example, a tetrafluoroethylene resin tube.

A fluid transfer tube 22 is axially movably inserted in the sheath 21. The fluid transfer tube 22 is also formed from a flexible tube such as a tetrafluoroethylene resin tube. A hollow needle 23 is firmly connected to the distal end of the fluid transfer tube 22. The needle 23 is made of an electrically conductive metal, e.g. a stainless steel. Accordingly, axially moving the fluid transfer tube 22 in the sheath 21 causes the needle 23 to project from or withdraw into the distal end of the sheath 21.

A stopper 24 formed from a metal ring is disposed on the inner surface of a distal end portion of the sheath 21 to prevent the needle 23 from excessively projecting from the distal end of the sheath 21. The needle 23 has a collar 23a projecting from the outer peripheral surface of its rear half. As shown in FIG. 2, when the collar 23a abuts on the stopper 24, the needle 23 projects from the distal end of the sheath 21 by a predetermined length but cannot project any further.

The distal end of the sheath 21 is drawn to reduce the inner diameter thereof so that the stopper 24 will not come off from the distal end of the sheath 21. A metallic reinforcing ring 29 is fitted and secured to the outer peripheral surface of the drawn distal end of the sheath 21.

An electrically conductive wire 30 is inserted in the fluid transfer tube 22. The electrically conductive wire 30 is formed from a metallic thin solid wire or stranded wire of good electrical conductivity. The distal end of the electrically conductive wire 30 is connected to a rear end portion of the needle 23.

Figure 3:
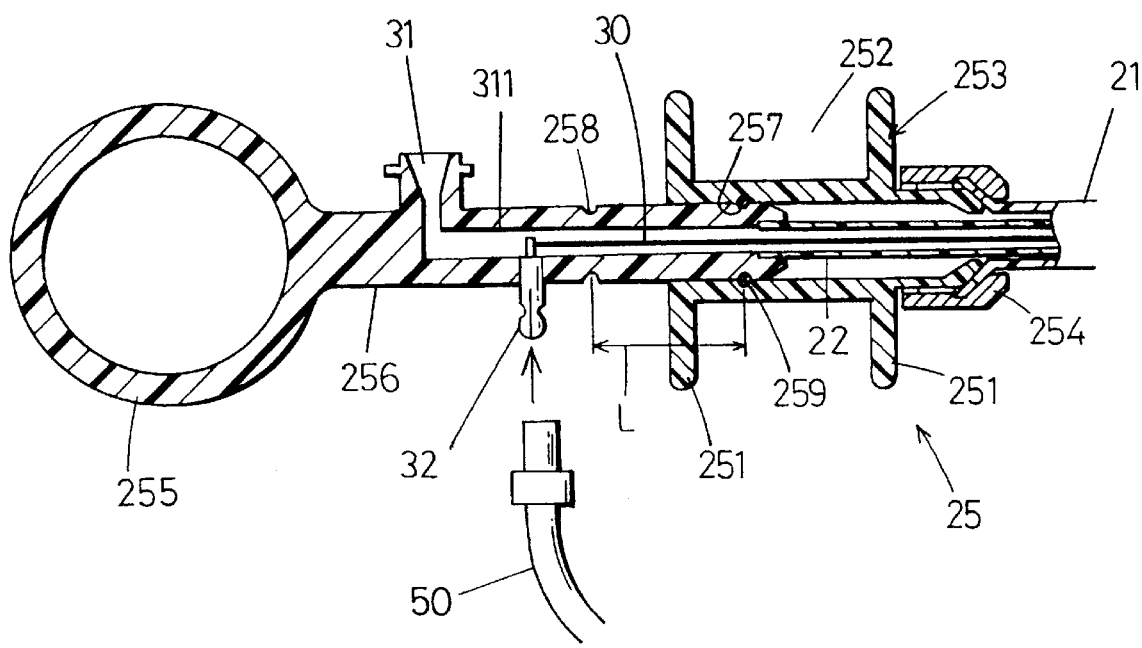
FIG. 3 is a sectional side view of an operating part of the syringe according to the first embodiment of the present invention.

FIG. 3 shows an operating part 25 connected to the proximal (rear) end of the sheath 21 to cause the fluid transfer tube 22 to move back and forth in the axial direction. The operating part 25 has a body 253 that has a pair of collars 251 and a spool-shaped finger engagement portion 252 formed therebetween. The proximal end portion of the sheath 21 is firmly connected to the operating part body 253 by using a retaining nut 254.

The inside of the operating part body 253 is a cylindrical hollow. A slider 256 has a rod-like portion at the distal end thereof and a ring-shaped finger engagement portion 255 at the proximal end thereof. The rod-like portion of the slider 256 is axially movably inserted in the operating part body 253.

The slider 256 is formed of an electrically insulating material. The outer peripheral surface of the proximal end of the fluid transfer tube 22 is rigidly secured to the distal end of the slider 256. A pair of circumferential grooves 257 and 258 are formed on the outer peripheral surface of the rod-like portion of the slider 256. The circumferential grooves 257 and 258 are a distance L away from each other. An elastic O-ring 259 is fitted in the inner peripheral surface of the operating part body 253. The O-ring 259 is engageable with either of the circumferential grooves 257 and 258.

Consequently, when actuating the slider 256 to move axially with the operator's fingers engaged with the two finger engagement portions, the operator feels a click at a position where the O-ring 259 engages with the circumferential grooves 257 or 258. Thus, the slider 256 is fixed relative to the operating part body 253 with some force.

Accordingly, the range of travel of the slider 256 in operation is from a position where the O-ring 259 engages with one circumferential groove 257 to a position where it engages with the other circumferential groove 258. The operating stroke of the slider 256 is L.

The operating stroke L of the slider 256 is preferably set slightly longer than the stroke of the needle 23 at the distal end of the sheath 21 in consideration of bending of the fluid transfer tube 22 in the sheath 21 when it is pushed from the operating part 25.

The slider 256 has a syringe tube receiving socket 31 (inlet port) and a connecting terminal 32, which project therefrom sideways. The syringe tube receiving socket 31 is communicated with the fluid transfer tube 22 through a liquid medicine passing bore 311 formed longitudinally in the slider 256.

Accordingly, if a syringe tube (not shown) is connected to the syringe tube receiving socket 31, a liquid medicine or the like can be sent to the needle 23 through the fluid transfer tube 22. It is also possible to suck a fluid into the fluid transfer tube 22 from the needle 23 and send it toward the syringe tube.

The proximal end of the electrically conductive wire 30, which is inserted in the fluid transfer tube 22 over the entire length thereof, is connected to the foot of the connecting terminal 32 in the liquid medicine passing bore 311. Accordingly, by connecting the connecting terminal 32 with a high-frequency power supply cord 50 connected to a high-frequency power supply (not shown), a high-frequency electric current can be sent to the needle 23 through the electrically conductive wire 30.

Figure 4:
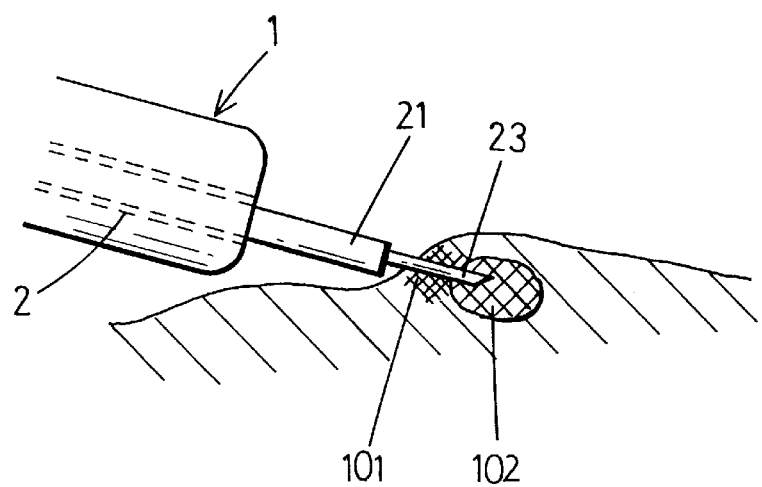
FIG. 4 is a schematic view showing the way in which the syringe according to the first embodiment of the present invention is actually used.

FIG. 4 shows the way in which the syringe arranged as stated above is actually used, which is inserted in an instrument-inserting channel 2 of an endoscope 1. The syringe according to the present invention is the same as the conventional syringes for endoscopes in terms of the procedure in which the distal end portion of the sheath 21 is projected from the endoscope 1, and the needle 23 is stuck into the affected part to inject a liquid medicine or to perform a suction treatment.

In use of the syringe according to the present invention, a high-frequency electric current is passed through the needle 23 before the needle 23 is pulled out from the mucous membrane upon completion of a treatment such as injection or suction. Consequently, as shown in FIG. 4, mucous membrane 101 around the needle 23 is cauterized and coagulated. Therefore, even when a thick blood vessel is stuck, it is possible to prevent bleeding from a hole opening after the needle 23 has been pulled out.

When an internal tumor or a cancer in mucous membrane is stuck with the needle 23, it is possible to perform a treatment in which such a diseased part 102 is cauterized and coagulated by using a high-frequency electric current.

Figure 5:
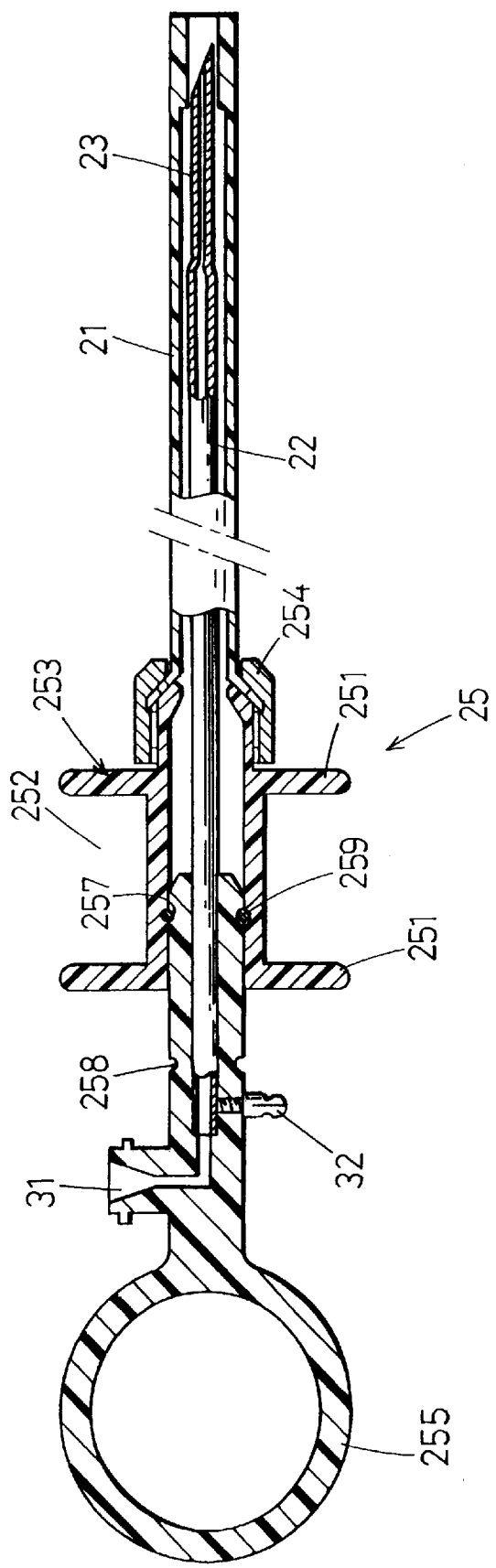
FIG. 5 is a sectional side view of a syringe for an endoscope according to a second embodiment of the present invention.

FIG. 5 shows a syringe for an endoscope according to a second embodiment of the present invention. The fluid transfer tube 22 and the needle 23 are integrally formed from a thin tube of an electrically conductive metallic material such as a titanium alloy, a stainless steel or a super elastic alloy, e.g. a nickel-titanium alloy. The fluid transfer tube 22 per se is used as an electrically conductive material that carries a high-frequency electric current, thereby simplifying the structure.

The fluid transfer tube 22 has a diameter of the order of from 1 millimeter to 2 millimeters. Therefore, reducing the wall thickness of the fluid transfer tube 22 makes it possible to obtain flexibility that enables the fluid transfer tube 22 to be removably inserted into the instrument-inserting channel of the endoscope. The proximal end of the fluid transfer tube 22 is connected directly to the connecting terminal 32. The arrangement of the rest of the second embodiment is the same as that in the first embodiment.

Figure 6:
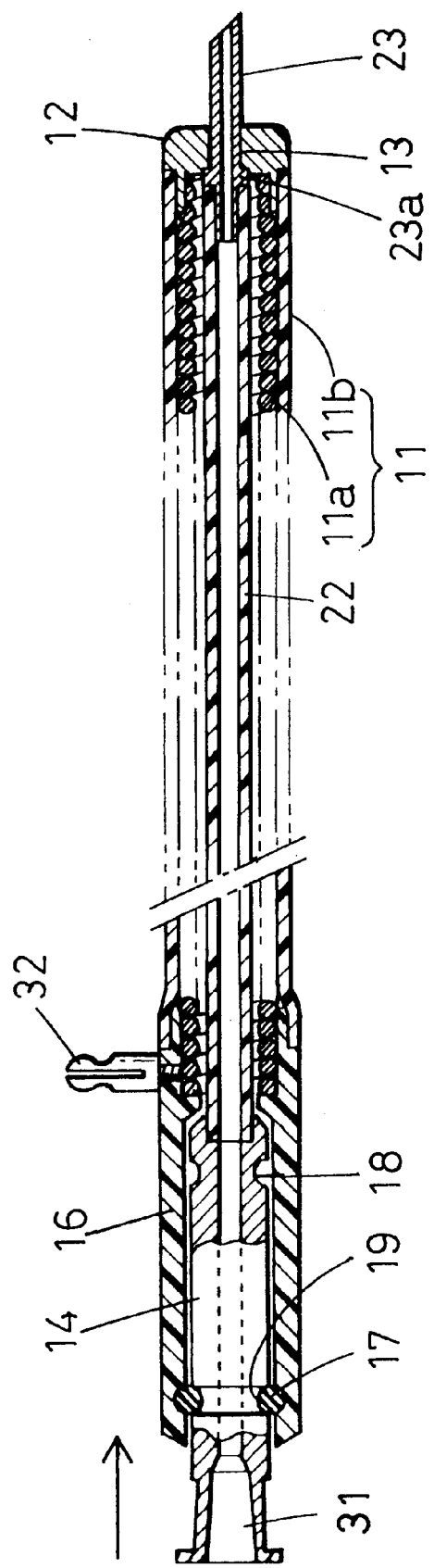
FIG. 6 is a sectional side view of a syringe for an endoscope according to a third embodiment of the present invention, showing a state where a needle projects from the distal end of a sheath.
Figure 7:
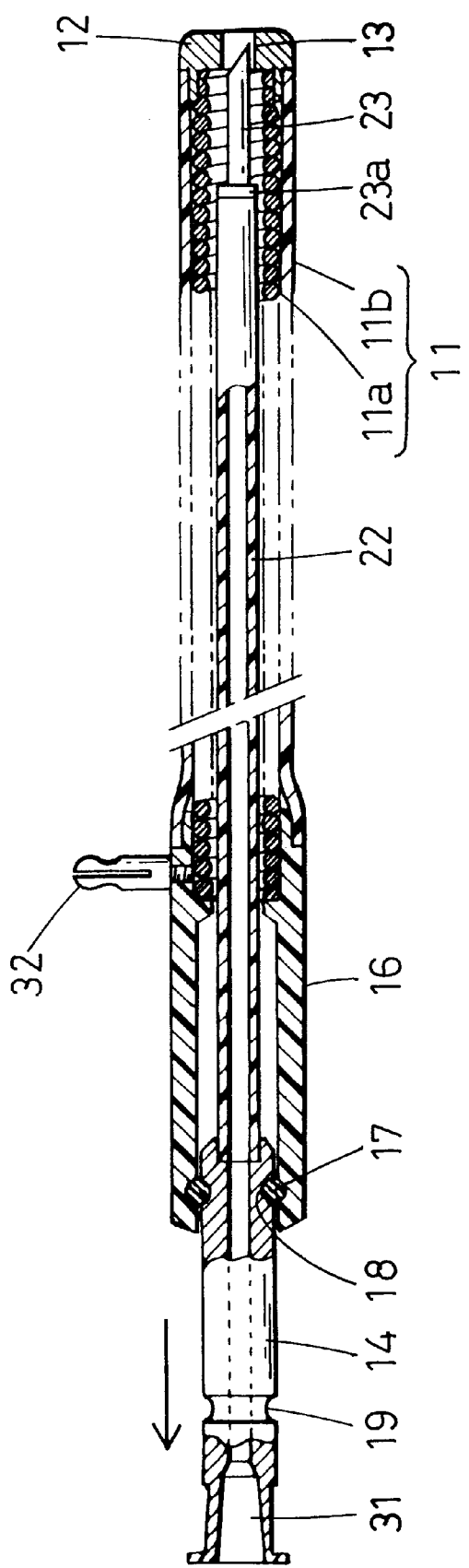
FIG. 7 is a sectional side view of the syringe according to the third embodiment of the present invention, showing a state where the needle is withdrawn into the distal end of the sheath.

FIGS. 6 and 7 show a syringe for an endoscope according to a third embodiment of the present invention. FIG. 6 shows the syringe in a state where a needle 23 projects from the distal end of a sheath 11. FIG. 7 shows the syringe in a state where the needle 23 is withdrawn into the sheath 11.

The sheath 11 in this embodiment has a coil pipe 11a formed by helically close-winding an electrically conductive metal wire, e.g. a stainless steel wire, with a uniform diameter. The outer surface of the coil pipe 11a is covered with a flexible electrically insulating tube 11b such as a tetrafluoroethylene resin tube.

A high-frequency electrode 12 is secured to the distal end of the sheath 11 in such a manner that the electrode 12 is exposed at the whole distal end surface of the sheath 11. The high-frequency electrode 12 is made of an electrically conductive metal, e.g. a stainless steel. The high-frequency electrode 12 is connected to the distal end portion of the coil pipe 11a by silver brazing or soldering. Thus, the two members are electrically connected to each other.

A fluid transfer tube 22 is axially movably inserted in the sheath 11. The fluid transfer tube 22 is an electrically insulating flexible tube such as a tetrafluoroethylene resin tube.

A hollow needle 23 made, for example, of a stainless steel is rigidly connected to the distal end of the fluid transfer tube 22. Accordingly, in response to an operation of axially moving the fluid transfer tube 22 in the sheath 11, the needle 23 projects from or withdraws into the distal end of the sheath 11 through a needle passing hole 13 provided in the high-frequency electrode 12 to extend therethrough at the axis position.

The needle 23 has a collar 23a formed on the outer peripheral surface of a portion thereof close to the rear end. The collar 23a has a diameter with which it cannot pass through the needle passing hole 13. When the collar 23a abuts on the reverse surface of the high-frequency electrode 12 as shown in FIG. 6, the needle 23 projects from the distal end surface of the high-frequency electrode 12 by a predetermined length but cannot project any further.

An inner tube 14 made of an electrically insulating plastic material is connected to the proximal end of the fluid transfer tube 22. The other end (rear end) of the inner tube 14 is provided with a syringe tube receiving socket 31. The inner tube 14 is axially movable in an outer tube 16 connected to the proximal end of the sheath 11. The outer tube 16 is made of an electrically insulating material.

An O-ring 17 is fitted in the inner periphery of the outer tube 16. The O-ring 17 engages with either of circumferential grooves 18 and 19 formed at two positions on the outer peripheral surface of the inner tube 14, thereby performing relative positioning between the inner and outer tubes 14 and 16.

In the state shown in FIG. 6, the O-ring 17 is engaged with the second circumferential groove 19, and the needle 23 projects from the distal end of the high-frequency electrode 12 by a predetermined length. In this state, an injection is given into the affected part.

In the state shown in FIG. 7, the O-ring 17 is engaged with the first circumferential groove 18, and the needle 23 is withdrawn into the sheath 11. In this state, the sheath 11 is inserted into or removed from an instrument-inserting channel of an endoscope.

A connecting terminal 32 is provided on the side surface of the outer tube 16. The connecting terminal 32 is connected to a high-frequency power supply cord (not shown). The connecting terminal 32 is screwed into the outer tube 16 such that the bottom of the connecting terminal 32 is in contact with the coil pipe 11a.

Accordingly, a high-frequency electric current can be sent from the connecting terminal 32 to the high-frequency electrode 12 through the coil pipe 11a. When projecting, the needle 23 comes into contact with the high-frequency electrode 12. Therefore, the high-frequency electric current also flows through the needle 23. However, there is no current leakage because the outer surface of the sheath 11 is covered with the electrically insulating tube 11b.

Figure 8:
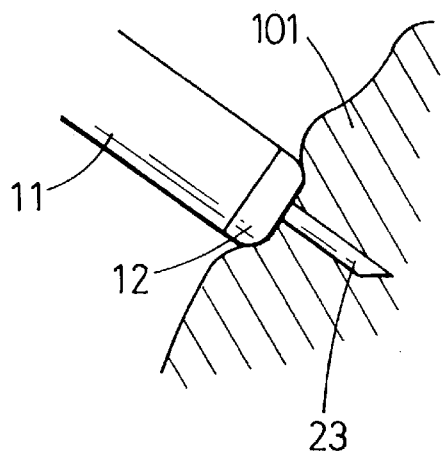
FIG. 8 is a schematic view showing the way in which the syringe according to the third embodiment of the present invention is actually used.

The syringe according to this embodiment, which is arranged as described above, is used as follows. First, as shown in FIG. 8, the needle 23 is stuck into mucous membrane 101 in a body cavity through an instrument-inserting channel of an endoscope (not shown) to give an injection of a liquid medicine, for example.

Figure 9:
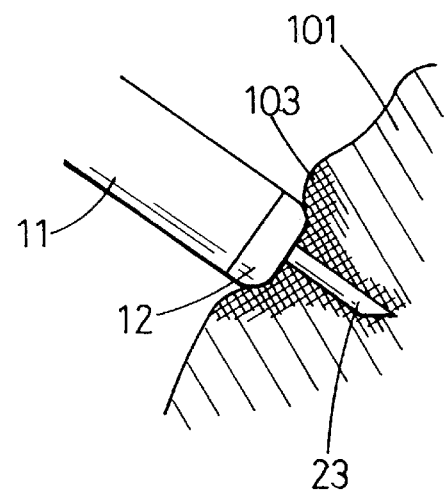
FIG. 9 is a schematic view showing the way in which the syringe according to the third embodiment of the present invention is actually used.

Before the needle 23 is pulled out from the mucous membrane 101, a high-frequency electric current is supplied to the high-frequency electrode 12, which is provided at the distal end of the sheath 11, with the electrode 12 placed in contact with the mucous membrane 101. Consequently, as shown in FIG. 9, the mucous membrane surface to which the high-frequency electrode 12 is applied is cauterized and coagulated by Joule's heat. Reference numeral 103 denotes the coagulated part. A portion that is contacted by the needle 23 is also coagulated.

Figure 10:
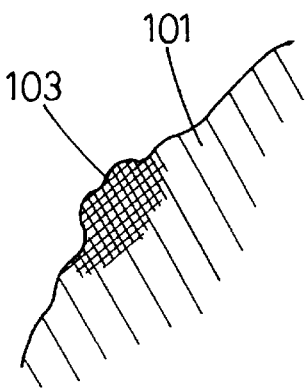
FIG. 10 is a schematic view showing the condition of a treated part after the use of the syringe according to the third embodiment of the present invention.

In this way, the hole through which the needle 23 is stuck and the mucous membrane 101 around the entrance of the hole are coagulated. Therefore, as shown in FIG. 10, there is no bleeding after the needle 23 has been pulled out from the mucous membrane 101. Thus, it is possible to prevent bleeding.

Figure 11:
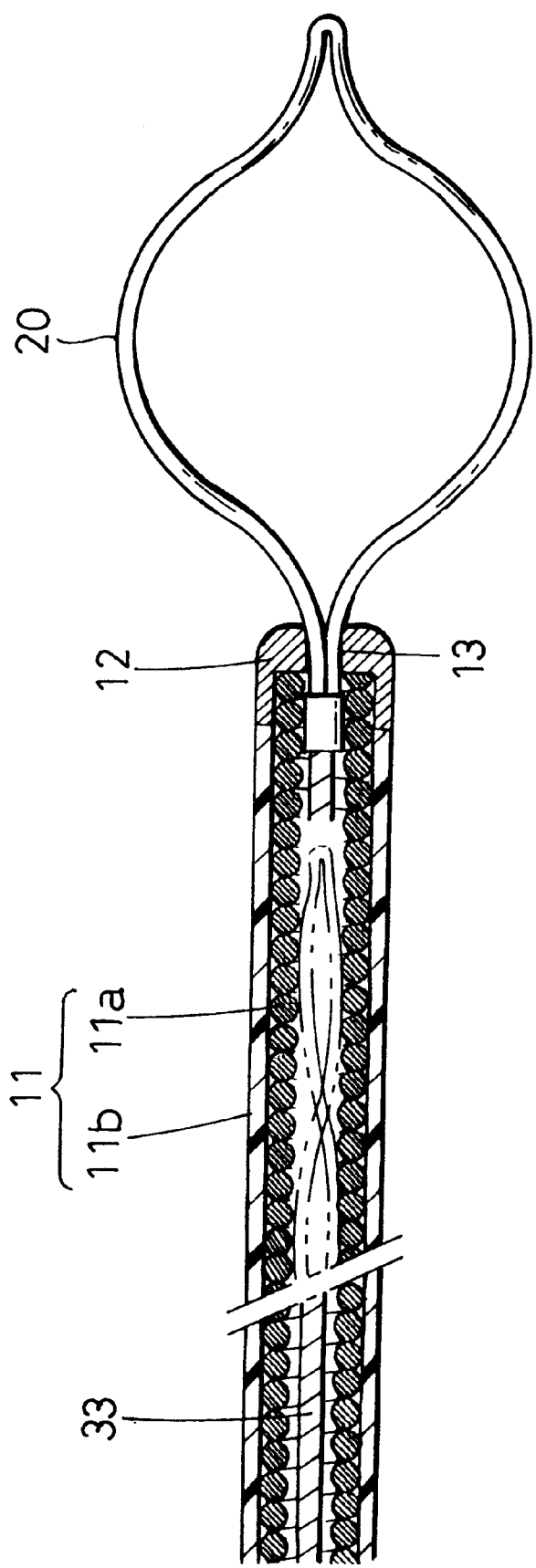
FIG. 11 is a sectional side view showing a distal end portion of a high-frequency snare for an endoscope according to a fourth embodiment of the present invention.
Figure 12:
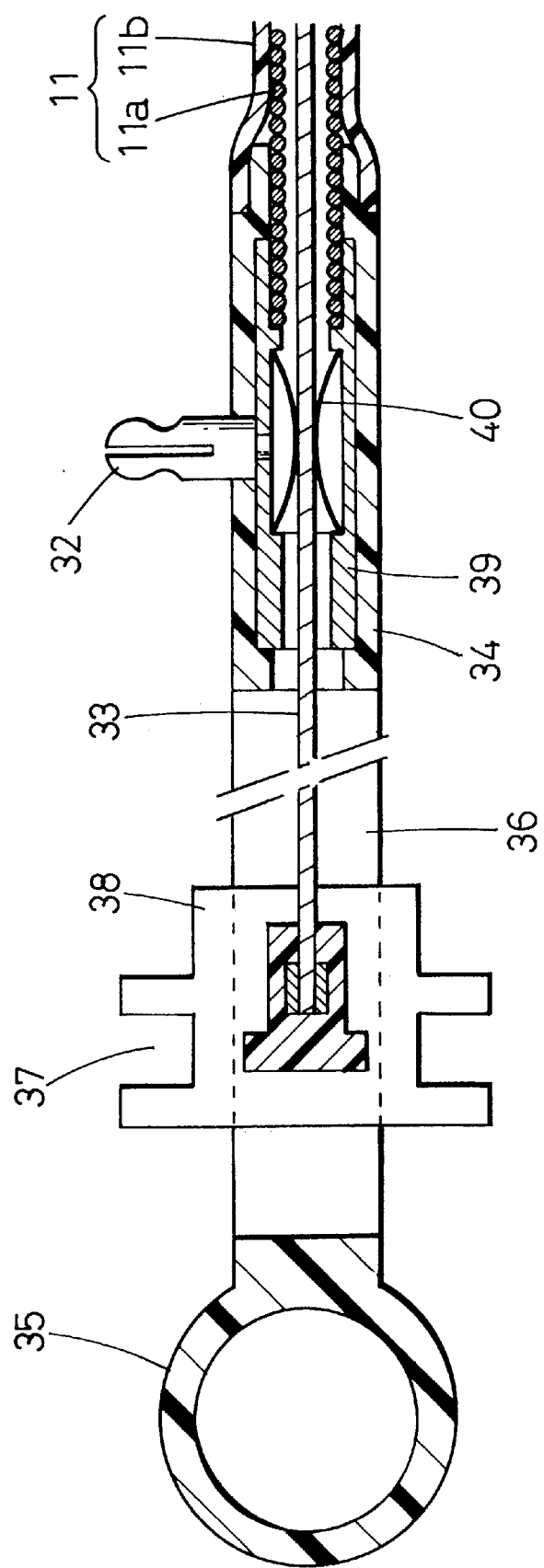
FIG. 12 is a sectional side view showing an operating part of the high-frequency snare according to the fourth embodiment of the present invention.

FIGS. 11 and 12 show a high-frequency snare for an endoscope according to a fourth embodiment of the present invention. FIG. 11 is a sectional side view showing a distal end portion of the high-frequency snare. FIG. 12 is a sectional side view showing an operating part of the high-frequency snare. A sheath 11 and a high-frequency electrode 12, which is secured to the distal end of the sheath 11, are arranged as in the case of the syringe according to the third embodiment.

As shown in FIG. 11, an electrically conductive control wire 33 is axially movably inserted in the sheath 11, and a snare wire 20 is connected to the distal end of the control wire 33. The snare wire 20 is an electrically conductive elastic wire.

Under free conditions, the snare wire 20 is expanded in a loop shape by its own elasticity. When withdrawn into the sheath 11 by the control wire 33, the snare wire 20 is elastically deformed to be folded as shown by the chain double-dashed line in FIG. 11.

As shown in FIG. 12, the operating part of the high-frequency snare has a body 34 formed of an electrically insulating plastic material. A ring-shaped finger engagement portion 35 is formed at the proximal end of the operating part body 34 to allow engagement with the operator's thumb.

In addition, a longitudinally elongated slit 36 is formed in the operating part body 34. A slider 38 is slidably fitted in the slit 36. The slider 38 is provided with a spool-shaped finger engagement portion 37 for engagement with the index and middle fingers. The proximal end of the control wire 33 is secured to the slider 38.

Accordingly, sliding the slider 38 along the slit 36 causes the control wire 33 to move axially and thus enables the snare wire 20 to be projected from and withdrawn into the distal end of the sheath 11.

A connecting tube 39 made of an electrically conductive metal is fixedly disposed in the operating part body 34 at a position where it surrounds the control wire 33. The proximal end of the coil pipe 11a is rigidly connected to the connecting tube 39. A connecting terminal 32 is fitted in the wide wall of the connecting tube 39 to project sideways from the operating part body 34.

Accordingly, the connecting terminal 32 and the high-frequency electrode 12 are electrically connected to each other through the connecting tube 39 and the coil pipe 11a. Thus, a high-frequency electric current can be sent to the high-frequency electrode 12 at the distal end of the sheath 11 through a high-frequency power supply cord connected to the connecting terminal 32.

Furthermore, leaf springs 40 made of an electrically conductive spring material are mounted on the inner surface of the connecting tube 39 to contact the surface of the control wire 33. Thus, the connecting terminal 32 and the control wire 33 are electrically connected through the connecting tube 39 and the leaf springs 40.

The control wire 33 is axially movable in contact with the leaf springs 40. Accordingly, a high-frequency electric current can be supplied to the snare wire 20 at the distal end of the sheath 11 at desired timing regardless of whether the snare wire 20 is expanded or contracted.

In actual use of the high-frequency snare for an endoscope arranged as stated above, first, a polyp, for example, is removed with the snare wire 20 as in the case of a conventional high-frequency snare for an endoscope.

Then, after the snare wire 20 has been withdrawn into the sheath 11, the sheath 11 is moved slightly forward to press the high-frequency electrode 12 against the cut surface of the mucous membrane from which the polyp has been excised. In this state, a high-frequency electric current is supplied to cauterize and coagulate the cut surface. Thus, it is possible to prevent bleeding from the cut surface after the removal of the polyp.

According to the present invention, an ordinary endoscopic treatment, e.g. injection into a body cavity or excision of a polyp, is performed with the treating instrument through an endoscope. Subsequently, the treated mucous membrane part is cauterized and coagulated by a high-frequency electric current using the treating instrument. Accordingly, it is possible to readily prevent bleeding after the endoscopic treatment.

While the invention has been described by reference to specific embodiments chosen for purposes of illustration, it should be apparent that numerous modifications could be made thereto by those skilled in the art without departing from the basic concept and scope of the invention.

What is claimed is:

1. A treating instrument for use with an endoscope, the treating instrument comprising:
    a flexible sheath configured to be removably inserted into an instrument-inserting channel of the endoscope, said sheath having an outer surface formed from an electrically insulating tube;
    a treating member configured to apply a treatment to mucous membrane in a body cavity, said treating member comprising a syringe needle, said syringe needle being formed from an electrically conductive material, and being projected from and withdrawn into a distal end of said sheath by an operation conducted at a proximal end of said sheath;
    an exposed electrode provided at a distal end surface of said sheath such that when said syringe needle is projected from the distal end of said sheath, said syringe needle contacts said exposed electrode; and
    an electrically conductive member extending through said sheath without electrically contacting a surface of said sheath, said electrically conductive member being electrically connected at a distal end to said electrode and connectable, at a proximal end, to a high-frequency power supply at the proximal end of said sheath.

2. A treating instrument according to claim 1, wherein said electrically conductive member is a metallic close-wound coil pipe that constitutes an inner part of said sheath, said coil pipe having an outer peripheral surface covered with said electrically insulating tube.

3. A treating instrument according to claim 1, further comprising:
    an operating member for actuating said treating member to project from and withdraw into the distal end of said sheath, said operating member being provided at the proximal end of said sheath,
    wherein said operating member is provided with a connecting terminal electrically connected to said electrically conductive member.

4. The treating apparatus according to claim 3, wherein said electrically conductive member comprises a metallic close-wound coiled pipe that constitutes an inner part of said sheath, said coiled pipe having an outer peripheral surface covered with said electrically insulating tube.

* * * * *